Figure 1:
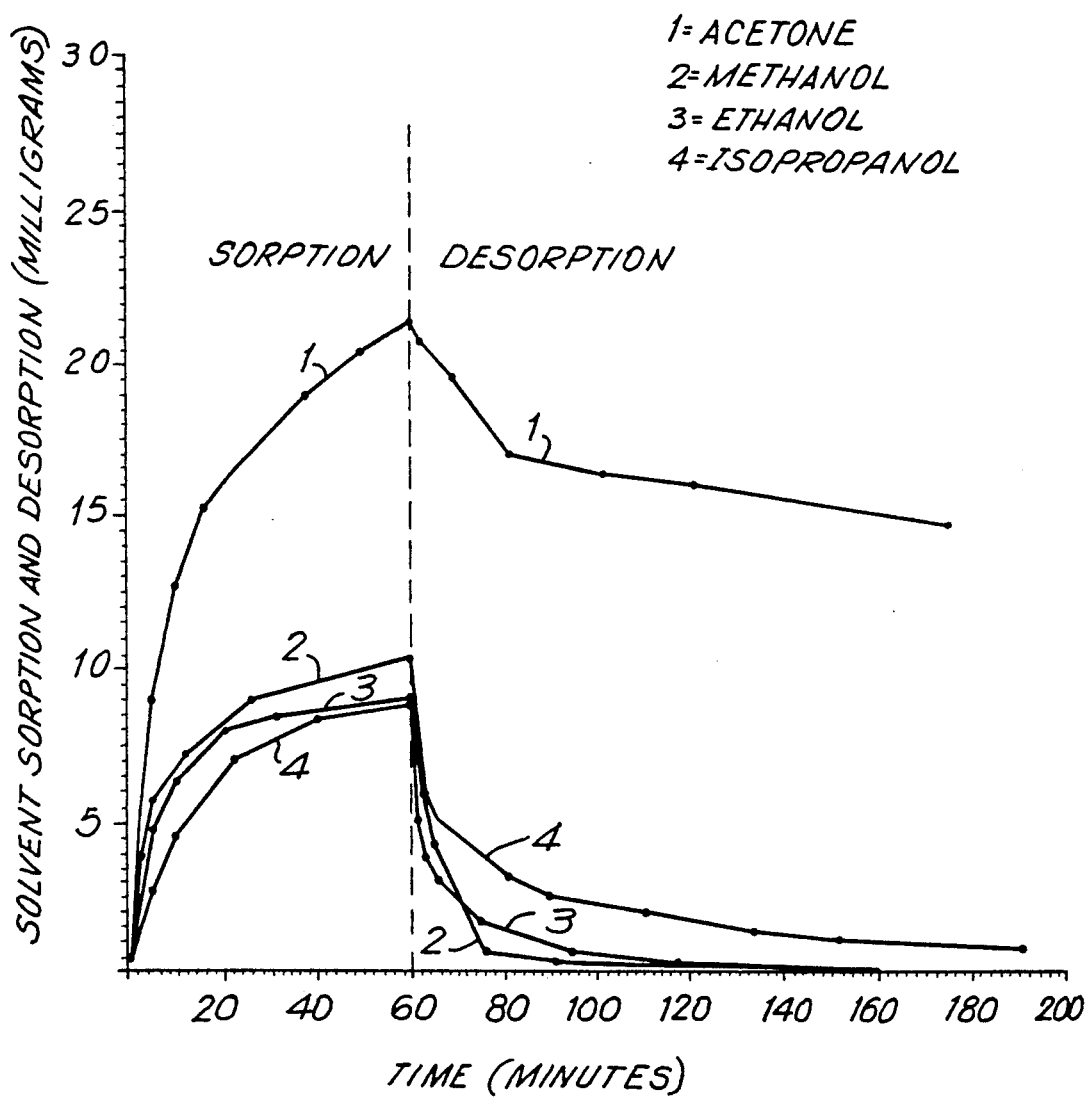

United States Patent [19]

Nuernberg et al.

[11] Patent Number: 5,011,694
[45] Date of Patent: Apr. 30, 1991

[54] PHARMACEUTICAL DOSAGE UNIT FORMS WITH DELAYED RELEASE

[75] Inventors: Eberhard Nuernberg, Uttenreuth-Weiher; Josef Pfeuffer, Bad Koenigshofen, both of Fed. Rep. of Germany

[73] Assignee: Röhm GmbH, Darmstadt, Fed. Rep. of Germany

[21] Appl. No.: 388,120

[22] Filed: Aug. 1, 1989

[30] Foreign Application Priority Data

Aug. 11, 1988 [DE] Fed. Rep. of Germany ....... 3827214

[51] Int. Cl.$^5$ ................................................ A61K 9/20
[52] U.S. Cl. ..................................... 424/464; 424/462; 424/468; 424/473; 424/81; 427/336
[58] Field of Search ............... 424/464, 462, 468, 473, 424/469, 81; 264/4.6, 4.33; 427/336

[56] References Cited

U.S. PATENT DOCUMENTS

| | | | |
|---|---|---|---|
| 2,987,445 | 6/1961 | Levesque | 167/82 |
| 3,087,860 | 4/1963 | Endicott | 167/82 |
| 3,148,124 | 9/1964 | Gaunt | 167/82 |
| 4,013,820 | 3/1977 | Farhadieh | 536/64 |
| 4,851,233 | 7/1989 | Khan | 424/480 |
| 4,853,249 | 8/1989 | Takashima | 427/3 |

FOREIGN PATENT DOCUMENTS 2187643  9/1987  United Kingdom .

OTHER PUBLICATIONS

Journal of Pharmaceutical Sciences, 60 (2), 212–215 (1971), Farhadieh et al., "Drug Release from Methyl-Acrylate-Methyl Methacrylate Copolymer Matrix II: Control of Release Rate by Exposure to Acetone Vapor".

Primary Examiner—Thurman Page
Assistant Examiner—D. Gabrielle Phelan
Attorney, Agent, or Firm—Curtis, Morris & Safford

[57] ABSTRACT

Improved delayed release pharmaceutical dosage unit forms such as tablets are obtained by exposing a matrix of a compressed mixture of active pharmaceutical ingredient and of a polyacrylic ester polymer or a vinyl ester polymer insoluble in body fluids at the point of release to vapors of a lower alcohol.

6 Claims, 3 Drawing Sheets

PHARMACEUTICAL DOSAGE UNIT FORMS WITH DELAYED RELEASE

The present invention relates to improved pharmaceutical dosage unit forms showing delayed release of active ingredient from a matrix and to a method for their preparation.

The treatment of a dosage unit form in such a way that it gives up the active ingredient to a surrounding physiological liquid more slowly than it does without such treatment is designated "retardation". In contrast to coated dosage unit forms in which a coating effects the delayed release of active ingredient, delayed release here involves the matrix itself and, as a result, is effective also for any fragments of the matrix.

If pharmaceutical dosage unit forms are pressed from a mixture of a powdered active ingredient and a powdered polymeric auxiliary, they release the active ingredient quickly in an aqueous medium. According to U.S. Pat. No. 3,087,860, the speed of release is delayed if one subjects such dosage unit forms to the vapors of an organic liquid which is a solvent for the auxiliary. The solvent is taken up by the auxiliary from the vapor phase and brings about the fusion of the particles of the polymeric auxiliary to form a coherent matrix which completely encloses the particles of the active ingredient. In the *Journal of Pharmaceutical Sciences*, Volume 60, 1971, pages 209-212, B. Farhadieh, S. Borodkin, and J. D. Buddenhagen have investigated this kind of matrix tablets which contained a methyl acrylate-methyl methacrylate copolymer as the auxiliary and which were treated with acetone vapors and determined a clear reduction in the speed of release.

However, the retardation method using acetone has several serious disadvantages. Thus, the delay effect has proved to be badly reproducible and changes on storage. Further, it is dependent on the size of the dosage unit forms treated and decreases within the dosage unit form from the outside towards the inside. This has the result that fragments of the treated dosage unit forms show a greater speed of release than undivided dosage unit forms. Further, it has proved difficult to remove the acetone from the treated dosage unit forms as thoroughly as is required by pharmacological demands for purity. This disadvantage is particularly severe for acetone, chlorohydrocarbons, or aromatics because they are not pharmacologically indifferent and are more or less toxic.

The problem underlying the present invention is to improve the known method for delaying release from dosage unit forms which contain a compressed matrix of powdered polymeric auxiliaries and active ingredients by the action of vapors of organic liquids thereon so that the mentioned disadvantages are avoided; a reproducible retardation, controllable through the duration of such action, is achieved in a relatively short treatment time; the organic liquid is rapidly desorbed from the treated dosage unit forms; and organic liquids of minimal toxicity can be used.

It has proved that this problem cannot be satisfactorily solved using good solvents for the auxiliaries, such as chloroform, dichloromethane, acetone, or toluene. Surprisingly, the lower alcohols give the desired effect although the auxiliaries from the group of acrylic polymers and vinyl ester polymers which are insoluble in stomach juice are often only swellable, but are not soluble or are only difficultly soluble, therein.

In the accompanying drawings, the advantage which can be attained by the invention is illustrated by a comparison of the action of various lower alkanols on a compressed matrix with that of acetone.

In the drawings, FIG. 1 shows the solvent sorption from the vapor phase in a pressed tablet of 8 mm diameter and 100 mg weight containing 10 percent of sodium chloride as the test active ingredient in a matrix of a copolymer of equal parts of methyl methacrylate and ethyl acrylate. The tablets are exposed to the solvent vapor for 60 minutes and subsequently dried. Acetone (Curve 1) is absorbed about twice as quickly as methanol (Curve 2), ethanol (Curve 3), and isopropyl alcohol (Curve 4), but on drying is only very slowly desorbed whereas the lower alcohols were removed almost completely within 1 to 2 hours. The remaining residue is—except for methanol—toxicologically harmless.

Figure 2:
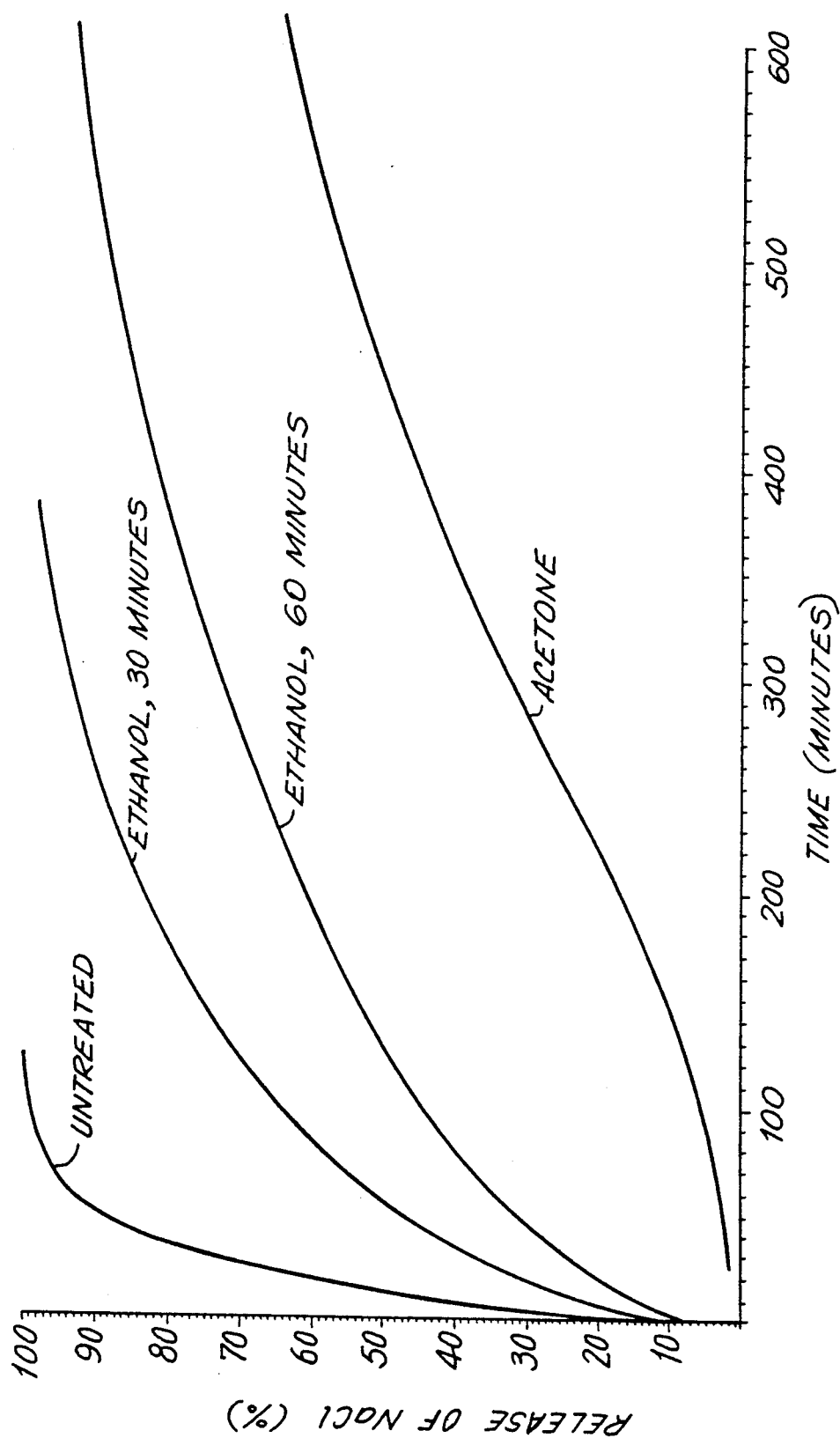

FIG. 2 shows the release of salt from tablets of the kind described which had been untreated, treated for 30 minutes, and treated for 60 minutes with ethanol vapor or for 15 minutes with acetone vapor. The untreated tablet releases the test agent undesirably quickly. By treatment with ethanol vapor for 30 or 60 minutes, a clearly graded retardation was effected with which a complete release of an active ingredient during the normal dwell time in the gastrointestinal tract can be brought about. In contrast, treatment with acetone vapor leads in just 15 minutes to such a strong retardation that a release of more than 50 percent of the active agent during passage through the stomach and intestine could hardly be achieved.

Figure 3:
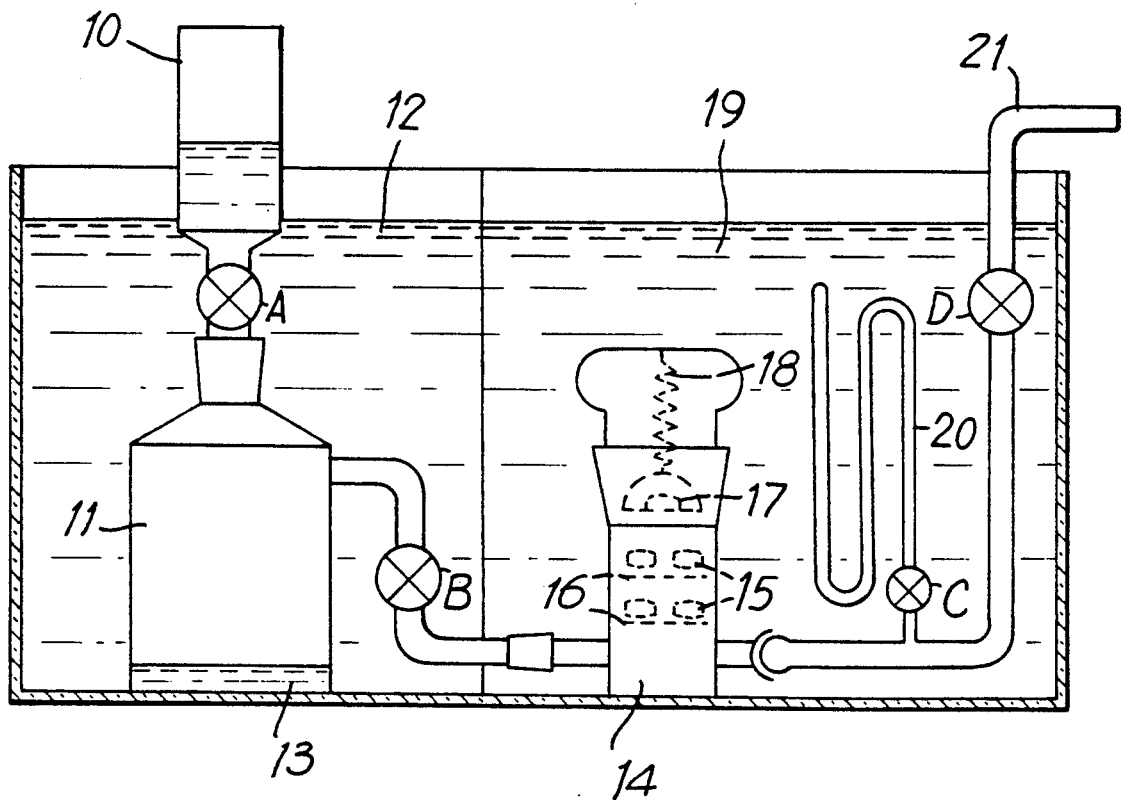

Finally, FIG. 3 shows an apparatus in which the method of the invention can be carried out. The apparatus comprises dropping funnel 10 in communication through valve A with solvent vapor generator 11 immersed in temperature controlled water bath 12 and containing lower alcohol 13. Generator 11 is in communication through valve B with incubation zone 14 which contains tablets 15 to be exposed to solvent vapors, suitably present on wire mesh screen 16. Further tablet or tablets 17 are suspended on spring scale 18, by observation of which the extent of uptake of solvent vapors by the tablets can be monitored. Incubation zone 14 is immersed in temperature controlled water bath 19 and is in communication through valve C with mercury manometer 20 and through valve D with vacuum line 21.

It appears that the only limited ability of the lower alcohols to dissolve the auxiliaries used is an important prerequisite for the effect observed. Acetone and chlorohydrocarbons, which are good solvents for the auxiliaries and which are recommended for this reason in U.S. Pat. No. 3,087,860, lead very quickly to a swelling, solution, and adhesion of the auxiliary particles. These flow together to form a closed layer that hinders the further penetration of the solvent vapor into the interior of the dosage unit form. In this way, a concentration gradient arises from the outside toward the inside which persists after the duration of treatment. After treatment is concluded, the solvent can only desorb in a limited way. In the course of time, the solvent concentration within the dosage unit form becomes uniform which, above all, has the undesired effect that the release behavior changes on storage.

In contrast, the particles of auxiliary are only swollen and softened by the penetrating vapors of lower alcohols so that they adhere to one another at opposed points of contact. The matrix formed by compression of the powdered starting materials remains porous during the vapor treatment, even if the pore size decreases. As a consequence, the alcohol vapor can flow in from the outside in the same measure that it can be absorbed in the interior. Because of the open pored structure, absorption takes place rapidly and extensively uniformly over the entire matrix of a dosage unit form. This is responsible for the advantages of the invention: There is no concentration gradient that can lead to a change in properties on storage. The consolidation of the matrix and the delay of release of the active ingredient caused thereby occur uniformly over the entire matrix, so that after the treatment fragments of the matrix, whether generated intentionally or unintentionally, show the same release characteristics—apart from a small effect due to the differing lengths of the diffusion paths—as the undivided dosage unit form. Desorption of the alcohol after treatment takes place as quickly and uniformly as before the absorption. Thus, the danger of impermissibly high solvent residues in the dosage unit forms of the invention is slight.

However, if alcohol residues remain in the dosage unit forms, this is as a rule harmless from the pharmacological point of view, particularly for the preferred ethyl alcohol, because of the slight toxicity of the alcohol. Only methanol is an exception in this regard.

As lower alcohols, the primary, secondary, or tertiary alkanols having 1 to 4, preferably 2 to 4, carbon atoms come into consideration. Propanol-1, propanol-2, n-butanol, butanol-2, tert-butanol, and particularly ethanol, are preferred.

It is advantageous if the gas phase with which the dosage unit forms are treated consists essentially only of the alcohol vapor. In this case, the gas phase flows into the pores of the dosage unit form in the same measure as the alcohol is absorbed in its interior. In contrast, if the gas phase contains significant amounts of non-absorbable inert gases, these accumulate in the pores and further alcohol vapor can then only flow into the pores by diffusion. In addition, the relatively slow diffusion processes which continue until a homogeneous equilibrium in the mixed gas phase is reached lead to problems of reproducibility. Thus, it is desirable to keep the fraction of the alcohol vapor in the gas phase as high as possible. In any case, the partial pressure of the alcohol should predominate. In practice, the alcohol portion, calculated on the partial pressure, is mostly in the range from 80 to 100 percent. Except for air, which can be completely excluded from the gas phase only with great technical effort, mainly water vapor is a minor component of the gas phase.

In contrast, the absolute pressure of the gas phase is of minor significance. For example, it can be in the range from 20 to 1000 millibars, or may even be greater. At low alcohol partial pressures, the same effect as at high partial pressures can be achieved by longer acting times for the vapor. To reach an advantageous alcohol partial pressure, the process can be carried out at elevated temperature. The preferred temperature region is between 18° C. and 50° C. The softening temperature of the auxiliary must be taken into account; a too-strong softening during absorption of the solvent vapor would be disadvantageous and can be avoided by use of a lower treatment temperature.

The polymeric auxiliary has the function of forming a solid compressed mass with the active ingredient when compressed, in which mass the auxiliary particles touch each other such that on treatment with alcohol vapor according to the invention they form a coherent but porous matrix. The auxiliary is so chosen that it is not dissolved in the body fluids with which the matrix is in contact during the time up to the release of the principal portion of the active ingredient. For orally administered dosage unit forms, this is the stomach juice and possibly the intestinal juice. As a rule it is not disadvantageous, or may even be advantageous, if the matrix dissolves after release of the predominant portion of the active ingredient. Thus, the auxiliary need not in every case be insoluble in lower portions of the intestinal tract. For dosage unit forms which are used in other body cavities, such as the oral cavity or in the eyelid, insolubility in the body fluids found there is sufficient.

Physiologically acceptable acrylic ester and vinyl ester polymers which are insoluble at least in stomach juice, but preferably also in intestinal juice, are used as auxiliaries. A property of these polymers which is important for the invention is their ability reversibly to absorb lower alcohols with swelling and softening.

As long as the matrix of the compressed mass according to the invention is undissolved, the active agent is released only by diffusion. In the case of an auxiliary insoluble in stomach juice and intestinal juice, the matrix appears externally unchanged after release of the active ingredient. A solution or swelling of the matrix in stomach juice or intestinal juice would influence the release characteristic and can be tolerated only to the extent that such changes are desired. If the matrix first becomes soluble at the increasing pH values in the lower intestinal tract, the active ingredient as a rule has already been released for the most part by diffusion. The release of the residue of the active ingredient then increases by the gradual solution of the matrix.

The preferred auxiliaries, insoluble in stomach and intestinal juice, are predominantly or completely comprised of acrylic esters or vinyl esters. As acrylic esters, above all the alkyl acrylates and alkyl methacrylates having 1 to 8, preferably 1 to 4, carbon atoms in the alkyl portion are suitable. Typical vinyl esters are those having 2 to 4 carbon atoms in the acid portion, such as vinyl acetate, vinyl propionate, and vinyl butyrate. The amount of acrylic ester or vinyl ester in the copolymers is at least 30, and preferable 50 to 100, percent by weight. To the extent that water insoluble comonomers such as styrene, ethylene, propylene, or vinyl chloride are used, the copolymer is insoluble in stomach and intestinal juice.

In contrast, copolymers soluble in intestinal juice are obtained if the copolymer is not crosslinked and comprises 30 to 70 percent by weight of comonomers having carboxyl or carboxylate groups. These include, for example, acrylic and methacrylic acid, maleic, fumaric, and itaconic acids. Hydroxyalkyl esters of acrylic or of methacrylic acid, particularly those having from 2 to 6 carbon atoms in the hydroxyalkyl portion, bring about solubility.

The auxiliary is used in the form of a compressible powder. The powder particles are preferably 50 to 250 microns in size. They can be obtained by grinding a bulk polymer or from an aqueous dispersion of an emulsion polymer by spray drying. Pearl polymers can optionally be used in unaltered form.

The active ingredient is also used in powder form, but can be present in coarser particle sizes, for example from 0.1 to 0.8 mm. The invention is suitable for every crystallized or amorphous active agent whose delayed release in the gastrointestinal tract is desired, and also for mixtures of active agents. Typical examples of such agents are acetylsalicylic acid, non-steroidal antirheumatics, antihypertensives, cardioglycosides, antiasthmatics, sedatives, stimulants, antibiotics, spasmolytics, hormones, and psychopharmaceuticals. The amount of the active agent can, e.g., be 1 to 90 percent by weight of the powder mixture to be compressed. Other further conventional additives can also be present in the powder mixture, such as highly dispersed silica gel, magnesium stearate, lactose, cellulose, calcium phosphate, talc, etc.; their amount may be, e.g., between 10 and 50 percent by weight. The mixture is compressed in known fashion, conventionally by pressure forces between 2 and 30 kiloNewtons, to compressed forms such as tablets or microtablets 0.1 to 30 mm in diameter.

The compressed forms are exposed according to the invention to a gas phase containing alcohol vapor. So that the gas phase can penetrate quickly and uniformly into the compressed form, it is advantageous first to expose it to a vacuum in order to draw air out of the pores and then to let the gas phase flow into the evacuated treatment zone. The vacuum treatment may optionally be repeated one or more times. To achieve a uniform retardation effect, care should be taken that all compressed forms are exposed in the same fashion to the gas phase. In a gas phase largely free of inert gas, this requirement is met for unagitated compressed particles in bulk, even when in large volume.

It is suitable to follow the progressing absorption of the alcohol vapor by the increase in weight and to terminate it when the desired degree of saturation is reached. It can be carried out to complete saturation, which is achieved when there is no further increase in weight. The adhesion of the auxiliary particles to form a porous matrix occurs concurrently with the absorption of the alcohol, but can also increase with time at an invariant degree of saturation.

Also temperature has a significant influence on the retardation effect. With increasing temperature, the polymeric auxiliary becomes softer and the vapor pressure of the alcohol becomes greater, whereby the effect is accelerated. If the compressed form has the same temperature as the gas phase and the treating apparatus, a readily reproducible result is achieved. If the compressed form is cooler than the gas phase, there may be a formation of condensate within the compressed particles and, as a result thereof, a non-uniform retardation effect over the cross section of the compressed mass. In order to suppress condensate formation, the gas phase can be kept at a temperature above the saturation point. In general, if there are temperature differences between the compressed mass, the apparatus, and the gas phase, there is always the danger of a non-uniform and difficultly reproducible action of the gas phase. Thus, low and uniform temperatures, particularly in the range from 18° C. to 50° C., are advantageous.

The treatment time as a rule is between 5 minutes and 24 hours, preferably from 20 to 60 minutes. After a sufficient action of the absorbed alcohol, the treatment is broken off by desorption. For this purpose, the treated compressed mass is advantageously exposed to a vacuum with gentle warming until the original weight is again nearly reached. A vacuum of 2 to 100 millibars and container temperatures of 20° C. to 70° C. are in general sufficient. The desorption often takes longer than the absorption, which is linked to the reduced pore volume. However, it is one of the advantages of the invention that desorption proceeds more quickly and completely than after the action of acetone or such good solvents.

During both absorption and also during desorption, it is advantageous to agitate the compressed forms in bulk continuously or intermittently, for example in a horizontally disposed rotating drum, by means of stirring paddles, or in a fluidized bed apparatus. However, in most cases, uniform results are obtained by storing the compressed forms in bulk on a suitable screen support without agitation.

The compressed form as a rule remains externally unchanged during the treatment of the invention. Also on the break surfaces of a compressed particle, the increasing "sintering" of the matrix is for the most part not observable. The strength of the compressed mass as a rule increases during the treatment. A reliable prediction concerning the retardation effect is only possible with a release test.

The apparatus used for vapor treatment in the following Examples is shown schematically in FIG. 3 and consists of a vapor generating unit 11 and an incubation zone 14 with a mercury manometer 20. All parts are fashioned from glass in order to enable an optical monitoring of the incubation process. The solvent vapor generator consists of a 100 ml glass flask with a ground glass connection to dropping funnel 10 and a second connection to incubation zone 14. Solvent vapor is generated by the introduction of 100 ml of the corresponding liquid 12. For this purpose, the apparatus is evacuated through line 21 and the degassed solvent is drawn out of the dropping funnel such that the entry of air is prevented. Since the vapor generating unit 11 in water bath 12 is maintained at 25° C., a saturated gas phase with the corresponding saturated vapor pressure of the solvent used is created so long as the latter is present in excess in the generating unit.

The temperature in the incubation zone 14 or in water bath 19 is chosen at 30° C., five degrees above that of the vapor generating unit, so that uncontrollable condensation phenomena caused by slight temperature variations, such as can arise when operating at vapor saturation, are avoided.

In incubation zone 14, the tablets 15 are exposed to the solvent vapor in a single layer on wire mesh 16 having an interior mesh opening of 1 mm.

For determination of the sorption and desorption cycles, a tablet 17 is always kept in a container on a spring scale 18.

After the two temperature baths 12 and 19 have reached their constant temperatures at 25°±0.5° C. or 30°±0.5° C., the following operating steps are taken one after the other:

Evacuation of the whole system with cut-off valve A closed (B, C, D open) through vacuum line 21 to a residual pressure below 1 Torr. In order to maintain constant any desorption processes possibly occurring on the tablets (e.g. air, water), the system is maintained in this condition for 30 minutes. At the same time the apparatus can be checked for tightness.

With valve B closed, a sufficient amount of degassed solvent kept at 25° C. is withdrawn from the dropping funnel by the vacuum while avoiding the entry of air. In the vapor generation unit, the saturation vapor pressure of the solvent at 25° C. establishes itself.

With valves A and D closed, B is opened to initiate the incubation period. Solvent vapor flows into the incubation zone and immediately the same vapor pressure as in the vapor generation unit is established.

At the end of the incubation period, valve B is closed and the incubation zone is evacuated.

After desorption of the solvent is concluded (monitoring by way of the desorption isotherm), the vacuum is broken and the tablets can be removed.

Under the conditions described above, the following saturation vapor pressures are established at 25° C. for the different solvents:

| Ethanol: | 58 ± 2 Torr |
|---|---|
| Isopropanol: | 44 ± 2 Torr |
| Acetone: | 222 ± 2 Torr. |

A better understanding of the invention and of its many advantages can be had from the following specific Examples, given by way of illustration.

EXAMPLE 1

A uniform powder mixture of
- 88 parts by weight (pbw) of a copolymer comprising equal parts by weight of methyl methacrylate and ethyl acrylate, as a spray dried emulsion polymer, particle size 2-20 microns;
- 2 pbw of highly dispersed silicon dioxide; and
- 10 pbw of salt (sodium chloride);

is compressed with 9 mm stamping dies under a pressure of 15 kN to form 100 mg tablets.

Release of salt from the treated tablets is tested in each case using two 100 mg tablets in 500 ml water at 37° C. in a US paddle apparatus at 50 rpm. In the following table are given the times, designated $t_{50\%}$ or $t_{90\%}$, after which 50% or 90% of the salt is released. Results:

| Treatment of the Tablets | $t_{50\%}$ | $t_{90\%}$ |
|---|---|---|
| Untreated | 10 min | 45 min |
| 30 min ethanol vapor | 55 min | 250 min |
| 60 min ethanol vapor | 125 min | 520 min |
| 15 min acetone vapor | 450 min | — |

EXAMPLE 2

The same powder mixture as in Example 1 was compressed with a 3 mm stamping die at 5 kN to form 7 mg tablets and some of the tablets were treated as before with ethanol vapor. The speed of release under the same testing conditions was:

| Treatment of the Tablets | $t_{50\%}$ | $t_{90\%}$ |
|---|---|---|
| Untreated | 5 min | 19 min |
| 120 min ethanol vapor | 87 min | 310 min. |

EXAMPLE 3

Tablets were prepared as in Example 1 from the following powder mixture:
- 50 pbw of a copolymer comprising 67 percent by weight of methyl methacrylate and 33 percent by weight of ethyl acrylate, 2-20 microns;
- 5 pbw of cellulose fiber;
- 0.5 pbw of magnesium stearate, 25-100 microns;
- 20 pbw of salicylic acid, 100-150 microns; and lactose hydrate, 25-250 micron, to 100 pbw.

For pressing, an 8 mm stamping die and a compression force of 10 kN were used. The tablet weight was 100 mg. After treatment with ethanol vapor as in Example 1, the release of the active ingredient was measured in a US paddle apparatus in acetate buffer at pH 5.0:

| Treatment of the Tablets | $t_{50\%}$ | $t_{90\%}$ |
|---|---|---|
| Untreated | 25 min | 90 min |
| 15 min ethanol vapor | 230 min | 480 min |
| 30 min ethanol vapor | 570 min | — |

EXAMPLE 4

Tablets were prepared as in Example 3 from a powder mixture of:
- 50 pbw of ethyl cellulose (viscosity of a 5% solution 45 mPa.s), commercially available as "Ethocel 45 cps";
- 10 pbw of a copolymer of 33 percent by weight of methyl methacrylate and 67 percent by weight of ethyl acrylate;
- 5 pbw of cellulose fiber;
- 0.5 pbw of magnesium stearate, 25-100 microns;
- 20 pbw tetracaine hydrochloride, 50-200 microns; and lactose hydrate, 25-250 microns, to 100 pbw.

Release of the active ingredient in water after ethanol vapor treatment as in Example 1:

| Treatment of the Tablets | $t_{50\%}$ | $t_{90\%}$ |
|---|---|---|
| Untreated | 18 min | 110 min |
| 30 min ethanol vapor | 32 min | 182 min |

EXAMPLE 5

A powder mixture of
- 97 pbw of the copolymer as in Example 1; and
- 3 pbw of pilocarpine hydrochloride, 100-450 microns was compressed with special kidney-shaped dies at a pressure of 10 kN to produce compressed forms weighing 10 mg and 0.3 mm in height for use in the eyelid and, again, some of the forms were treated with ethanol vapor. Release in water gave:

| Treatment of the Tablets | $t_{50\%}$ | $t_{90\%}$ |
|---|---|---|
| Untreated | 3 min | 8 min |
| 30 min ethanol vapor | 35 min | 180 min |

EXAMPLE 6

A dispersion of 80 parts by weight of the copolymer of Example 1 and 20 parts by weight of sodium chloride were spray dried and the powder obtain was compressed with 8 mm dies at a pressure of 10 kN to produce 100 mg compressed forms. Release testing in water gave:

| Treatment of the Tablets | $t_{50\%}$ | $t_{90\%}$ |
|---|---|---|
| Untreated | 40 min | 170 min |
| 30 min isopropanol vapor | 90 min | 300 min |
| 60 min isopropanol vapor | 110 min | 360 min |

EXAMPLE 7

A powder mixture composed of
- 79.6 parts by weight (pbw) of a copolymer powder comprising 65 percent by weight of methyl methacrylate; 30 percent by weight of ethyl acrylate; 5 percent by weight of trimethylammoniumethyl methacrylate chloride;
- 0.4/pbw of talcum; and
- 20.0 pbw of sodium salicylate was compressed to tablets having a diameter of 3 mm, applying a pressure of 5 kN. The tablets were exposed to ethanol vapor for one to six hours, respectively. The release of sodium salicylate in pure water at 37° C. under gently stirring (50 rpm) was determined from the UV extinction at 296 nm:

| Ethanol vapor treating period: | 0 | 1 | 2 | 4 | 6 | hours |
|---|---|---|---|---|---|---|
| Release of sodium salicylate within two hours (percent of total content) | 100 | 97 | 90 | 80 | 60 | % |
| 90% release after | 15 | 40 | 120 | 240 | 550 | minutes |

Example 8

A powder mixture composed of
- 50.0 pbw of a copolymer powder comprising 33 percent by weight of methacrylic acid; 67 percent by weight of methyl methacrylate;
- 5.0 pbw of cellulose fibers
- 24.5 pbw of lactose hydrate
- 0.5 pbw of magnesium stearate
- 20.0 pbw of salicylic acid was compressed to tablets having a weight of 12.5 mg and a diameter of 3 mm. The tablets were exposed to ethanol vapor for one or two hours, respectively. Release of sodium salicylate was determined as in Example 7.

| Ethanol vapor treating period: | 0 | 0.5 | 1 | hours |
|---|---|---|---|---|
| 75% release of salicylic acid | | | | |
| (a) in acetate buffer of pH 5.0 after | 80 | 160 | 550 | minutes |
| (b) in phosphate buffer of pH 7.4 after | 45 | 85 | 280 | minutes |

What is claimed is:

1. A method for making a delayed release pharmaceutical dosage unit form which comprises contacting, at a temperature from 18° C. to 50° C. and for a time between 5 minutes and 24 hours, a gas phase comprising the vapor of a lower alcohol having 1 to 4 carbon atoms with a matrix which comprises a compressed mixture of a powdered active pharmaceutical and a powdered polymer selected from the group consisting of polymers of acrylate esters, polymers of methacrylate esters, and vinyl ester polymers.

2. A method as in claim 1 wherein said powdered polymer comprises at least 30 percent by weight of an alkyl ester of acrylic acid or of an alkyl ester of methacrylic acid having from 1 to 8 carbon atoms in the alkyl portion and up to 70 percent by weight of a different $\alpha,\beta$- ethylenically unsaturated comonomer.

3. A method as in claim 2 wherein said powdered polymer comprises a comonomer selected from the group consisting of acrylic acid, methacrylic acid, and hydroxyalkyl esters of said acids wherein the hydroxyalkyl portion contains 2 to 6 carbon atoms.

4. A method as in claim 1 wherein said lower alcohol is ethanol.

5. A method as in claim 1 wherein said matrix additionally comprises a further polymer, difficultly soluble in water and stomach juice, different from said powdered polymer.

6. A method as in claim 5 wherein said further polymer is ethyl cellulose.

* * * * *